(12) United States Patent
Taneda

(10) Patent No.: US 11,721,368 B2
(45) Date of Patent: Aug. 8, 2023

(54) RADIOGRAPHIC IMAGE PROCESSING APPARATUS, RADIOGRAPHIC IMAGE PROCESSING METHOD, AND STORAGE MEDIUM

(71) Applicant: Konica Minolta, Inc., Tokyo (JP)

(72) Inventor: Atsushi Taneda, Koganei (JP)

(73) Assignee: KONICA MINOLTA, INC., Tokyo (JP)

( * ) Notice: Subject to any disclaimer, the term of this patent is extended or adjusted under 35 U.S.C. 154(b) by 0 days.

(21) Appl. No.: 17/389,916

(22) Filed: Jul. 30, 2021

(65) Prior Publication Data
US 2022/0036924 A1     Feb. 3, 2022

(30) Foreign Application Priority Data

Jul. 31, 2020 (JP) .................................. 2020-129796

(51) Int. Cl.
| | | |
|---|---|---|
| G11B 27/10 | (2006.01) | |
| H04N 7/01 | (2006.01) | |
| A61B 6/00 | (2006.01) | |
| G11B 20/00 | (2006.01) | |

(52) U.S. Cl.
CPC .............. *G11B 27/10* (2013.01); *A61B 6/461* (2013.01); *A61B 6/56* (2013.01); *G11B 20/00007* (2013.01); *H04N 7/0127* (2013.01); *G11B 2020/00072* (2013.01)

(58) Field of Classification Search
CPC . G11B 20/00007; G11B 27/031; G11B 27/10; G11B 2020/00072; A61B 6/461; A61B 6/56; H04N 7/0127
USPC ................ 386/224, 223, 226, 227, 230, 210
See application file for complete search history.

(56) References Cited

FOREIGN PATENT DOCUMENTS

| | | | |
|---|---|---|---|
| JP | 2007268154 A | 10/2007 | |
| JP | 4408555 B2 | * | 2/2010 |

* cited by examiner

*Primary Examiner* — Loi H Tran
(74) *Attorney, Agent, or Firm* — Cantor Colburn LLP

(57) ABSTRACT

A radiographic image processing apparatus includes a hardware processor and an image processor. The hardware processor obtains moving image data captured by a radiographic imaging apparatus, causes a display to display a moving image based on the moving image data, and specifies a part of the moving image data that is to be output to an external device. The image processor performs image processing on the part of the moving image data. The hardware processor outputs, to the external device, the part of the moving image data on which the image processing has been performed by the image processor.

11 Claims, 5 Drawing Sheets

RADIOGRAPHIC IMAGE PROCESSING APPARATUS, RADIOGRAPHIC IMAGE PROCESSING METHOD, AND STORAGE MEDIUM

CROSS-REFERENCE TO RELATED APPLICATIONS

The present invention claims priority under 35 U.S.C. § 119 to Japanese Patent Application No. 2020-129796 filed on Jul. 31, 2020, the entire content of which is incorporated herein by reference.

BACKGROUND

Technological Field

The present disclosure relates to a radiographic image processing apparatus, a radiographic image processing method, and a storage medium.

Description of Related Art

Dynamic imaging is a method of taking a moving image (dynamic image) by consecutively taking still images. Dynamic imaging is used for obtaining the dynamic state of the lungfield to evaluate its functions, for checking the lumbar spines in orthopedics, and for checking the motion ranges of the legs and arms. In orthopedics, taken images are directly stored as they are in the picture archiving and communication systems (PACS) and viewed on the Web so that the motion ranges are checked in a moving image.

Dynamic imaging, in which still images are consecutively taken, generates a large volume of data. While the data volume of a still image is several to several tens megabytes (MB), the data volume of a dynamic image is several gigabytes (GB).

In the known art, predetermined image data generated in an examination (e.g., only obtained moving images) may be automatically stored in a medium or sent to an image server at the end of imaging/examination in order to reduce time and work of an operator.

However, when the predetermined image data is automatically stored in the external medium, image data that the operator considers unnecessary may also be automatically stored. For example, a catheter for injecting a contrast medium may bounce up just after the imaging starts, and a region of interest may not be contrasted. In such a case, the imaging has to be stopped immediately and the operator may determine not to store the interrupted image data in the medium. The image data, however, may be automatically stored in the medium. When the medium is a CD-ROM, the recorded data cannot be deleted, and unnecessary data is kept recorded.

To deal with such issues, JP2007-268154A discloses a method for avoiding recording unnecessary images. According to JP2007-268154A, images that meet certain criteria are extracted from obtained images and are temporarily stored in an external image memory. Among the temporarily stored images, user selects necessary images to be recorded.

SUMMARY

However, according to JP2007-268154A, images to be output to the external image memory are processed before the user selects necessary images. This does not reduce the load of image processing.

Objects of the present invention include providing a radiographic image processing apparatus, a radiographic image processing method, and a storage medium that can more efficiently output moving image data obtained by a radiographic imaging apparatus to external devices.

To achieve at least one of the abovementioned objects, according to an aspect of the present invention, there is provided a radiographic image processing apparatus including: a hardware processor that obtains moving image data captured by a radiographic imaging apparatus, causes a display to display a moving image based on the moving image data, and specifies a part of the moving image data that is to be output to an external device; and an image processor that performs image processing on the part of the moving image data, wherein the hardware processor outputs, to the external device, the part of the moving image data on which the image processing has been performed by the image processor.

According to another aspect of the present invention, there is provided a radiographic image processing method including: obtaining moving image data captured by a radiographic imaging apparatus; causing a display to display a moving image based on the moving image data; specifying a part of the moving image that is to be output to an external device; performing image processing on the part of the moving image data; and outputting, to the external device, the part of the moving image data on which the image processing has been performed.

According to another aspect of the present invention, there is provided a non-transitory computer-readable storage medium storing a program that causes a computer of a radiographic image processing apparatus to: obtain moving image data captured by a radiographic imaging apparatus; cause a display to display a moving image based on the moving image data; specify a part of the moving image that is to be output to an external device; perform image processing on the part of the moving image data; and output, to the external device, the part of the moving image data on which the image processing has been performed.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention, wherein.

DETAILED DESCRIPTION OF THE EMBODIMENTS

Hereinafter, one or more embodiments of the present invention will be described in detail with reference to the drawings. However, the scope of the invention is not limited to the disclosed embodiments.

Figure 1:
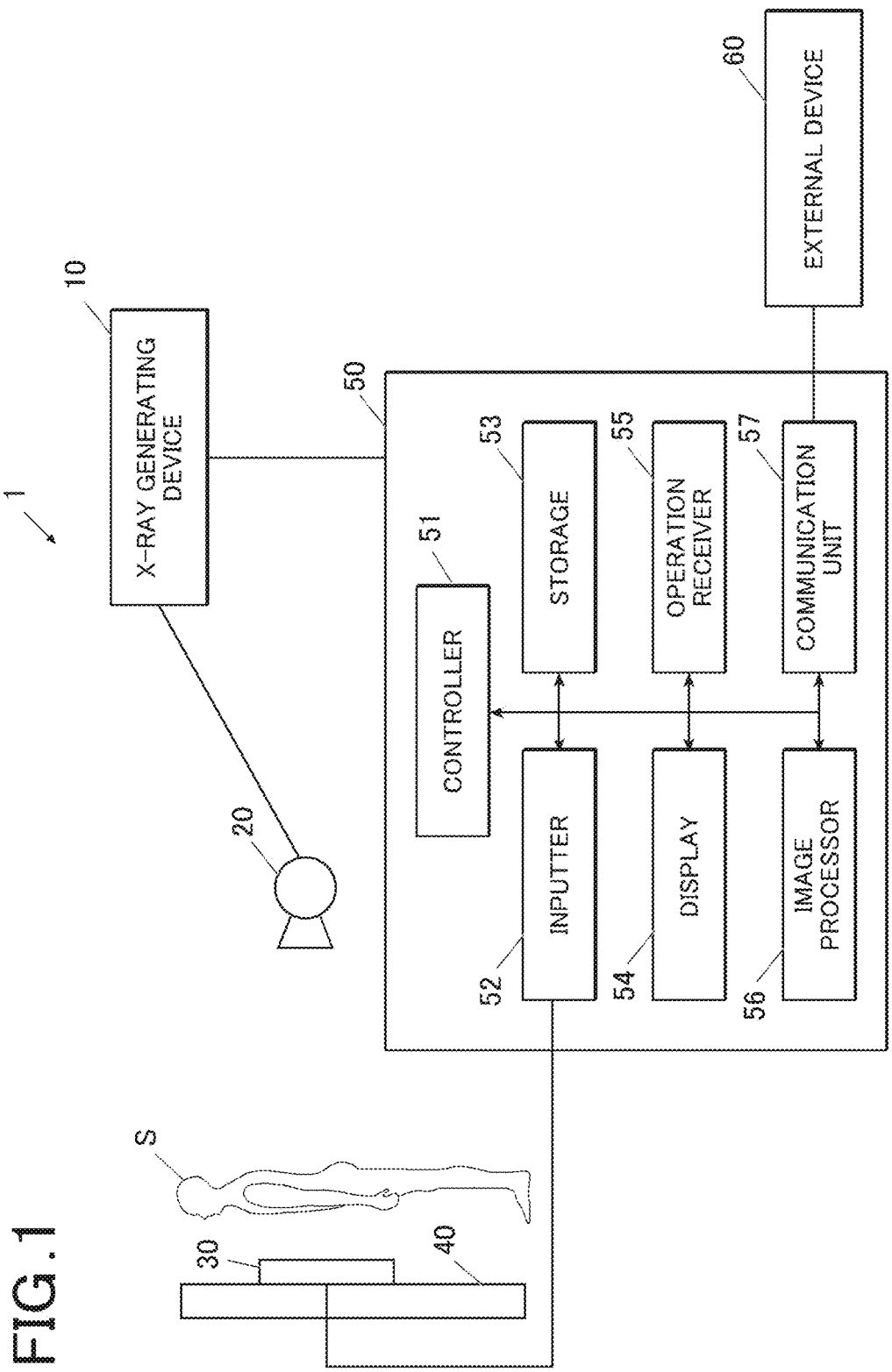
FIG. 1 shows a configuration of an X-ray imaging system that includes a radiographic image processing apparatus according to an embodiment of the present invention.

FIG. 1 shows main components of an X-ray imaging system 1 according to an embodiment of the present invention. As shown in FIG. 1, the X-ray imaging system 1 includes an X-ray generating device 10, a flat panel detector (FPD) 30, and a console 50. The X-ray generating device 10 includes an X-ray emitter 20 (not shown) to irradiate a subject with X-rays. The FPD 30 detects X-rays with which the subject is irradiated and generates radiographic images (captured images). The console 50 processes and displays the radiographic images output by the FPD 30.

The X-ray emitter 20 of the X-ray generating device 10 is a known X-ray tube (vacuum tube, not shown). The X-ray generating device 10 further includes a power supply that applies voltage to the X-ray tube and a controller that controls the power supply. The power supply includes: a filament power supply that heats filaments mounted on the negative electrode of the X-ray tube; and a high-voltage power supply that increases the speed of electrons striking the target on the positive electrode of the X-ray tube. The X-ray generating device 10 regulates X-rays emitted from the X-ray tube by controlling the filament power supply and the high-voltage power supply.

The FPD 30 detects X-rays that are emitted from the X-ray emitter 20 of the X-ray generating device 10 and that hit a region of the subject S, and outputs the detected X-rays as an electronic image (X-ray image, captured image). The FPD 30 thus functions as a radiographic imaging apparatus. The FPD 30 includes a not-shown sensor panel in which radiation detecting elements are arranged two-dimensionally in a matrix of n×m. The sensor panel detects X-rays that hit the region of the subject S. The FPD 30 further includes: a converter that converts the detected X-rays into electric signals; an A/D converter that digitizes the electric signals; and an outputter that outputs the digitized signals to the console 50 (computer for display) as captured images. In this embodiment, the sensor panel of the FPD 30 is placed to be substantially orthogonal to the direction in which X-rays are emitted from the X-ray emitter 20.

In this embodiment, the console 50 is placed in a room different from the room in which the X-ray generating device 10, the FPD 30, and an imaging stand 40 are placed. The console 50 controls radiographic imaging, performs processing on the obtained radiographic image data, and so forth. The console 50 functions as a radiographic image processing apparatus in the present invention. The console 50 includes a controller 51 (hardware processor), an inputter 52, a storage 53, a display 54, an operation receiver 56, an image processor 56, and a communication unit 57.

The controller 51 functions as: an obtaining unit that obtains the radiographic image data from the FPD 30 via the inputter 52: a display control unit that controls the contents displayed on the display 54; a specifying unit that receives from the operation receiver 55 operation signals specifying the part of the radiographic image data to be output (to-be-output part) and specifies the to-be-output part of the image data stored in the storage 53; and an output control unit that outputs the image data to an external device 60 via the communication unit 57. The method of specifying the to-be-output part by the operator is described later.

The controller 51 includes a central processing unit (CPU) as an arithmetic/control unit, a read only memory (ROM) as a main storage, and a random access memory (RAM), which are not shown. The ROM stores basic programs and setting data. The CPU reads a program for a process to be performed in the storage 53 or the ROM, loads the program into the RAM, and executes the loaded program, thereby centrally controlling the operation of the components of the console 50, such as the FPD 30.

The inputter 52 is an interface that inputs the image data output by the FPD 30 into the console 50.

The inputter 52 is connected to the FPD 30 via wired/wireless connection and inputs the image data to the console 50. The inputter 52 may be a communication interface for a near-field wireless communication, such as a near field communication (NFC) or Bluetooth (registered trademark).

The storage 53 stores all the image data that the controller 51 obtains from the FPD 30 via the inputter 52. That is, in the present disclosure, the image data is obtained from the FPD 30 and stored without being narrowed down. The storage 53 also stores image data that is not included in the to-be-output part.

This allows the operator who wrongly specified the to-be-output part to re-specify the to-be-output part.

The storage 53 is an auxiliary storage that consists of a hard disk drive (HDD) or a solid state drive (SSD), for example. The storage 53 may be a disc drive that drives an optical disc, such as a compact disc (CD) or a digital versatile disc (DVD), and/or a magneto-optical (MO) disc for reading and writing information. The storage 53 may also be a memory card, such as a USB memory or a secure digital (SD) card.

The image data may be stored in the RAM of the controller 51 during the examination and then stored in the storage 53 after the examination.

This allows the image data to be quickly read during the examination and retained after the examination ends and the console 50 is switched off.

The controller 51 may be configured to delete image data according to the free space of the storage 53 and the duration for which the image data has been maintained in the storage 53.

This can optimize the system of the console 50.

The display 54 includes, for example, a liquid crystal display (LCD). The display 54 displays various images including the obtained images under the control of the not-shown CPU.

The operation receiver 55 includes a pointing device, such as a mouse, a keyboard with cursor keys, number input keys and various function keys. The operation receiver 55 receives operation signals input by key operation or mouse operation and outputs the signals to the controller 51.

The display 54 and the operation receiver 55 may be formed as one body, such as a liquid crystal display with a touchscreen.

In externally recording the image data, the image processor 56 performs processing on part of the image data that is determined to be output by the controller 51.

That is, the image processor 56 performs processing on only the part of the image data that the operator considers necessary for diagnosis. This reduces system load.

Examples of image processing in externally recording the image data include smoothing of images. When the smoothing of one image takes 0.1 second, the smoothing of 100 images takes 10 seconds. When the operator reduces the number of images to 50 by selecting the part considered to be necessary for diagnosis, the time required for smoothing is shortened by 5 seconds. This can reduce system load.

The image processor 56 can also generate a compressed moving image into which the specified image part is compressed in a video file format. The image processor 56 can output the moving image data in a common video file format, such as MP4, not in the DICOM format. The image data in the MP4 format can be used for conferences, for example. With image data output in various formats, users can review necessary part of images for various purposes.

In outputting image data, the image processor 56 performs different kinds of processing on image data for display and image data specified by the controller 51. Processing multiple frames places heavy loads on the system. In the case, the image processor 56 performs light processing on image data for display to maintain readiness.

The communication unit 57 is connected to the external device 60 via wired/wireless connection and outputs image data to the external device 60. For example, the communication unit 57 exchanges various kinds of information with the external device 60 over a wired/wireless communication network in accordance with the DICOM standard. The communication unit 57 may be a communication interface for a near-field wireless communication, such as a near field communication (NFC) or Bluetooth (registered trademark).

The external device 60 is, for example, a PACS, a hospital information system (HIS), or a radiology information system (RIS). X-ray images can be permanently stored in external recording media, such as image servers with mass storage or CD-ROMs.

<To-Be-Output Image Generating Process>

Figure 2:
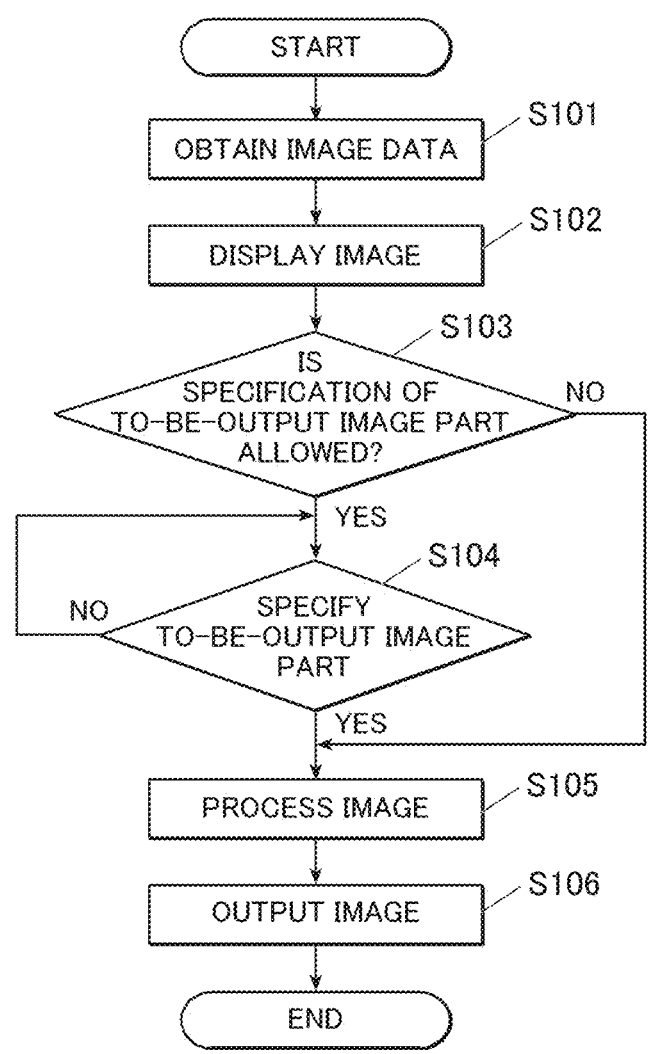
FIG. 2 shows a flow of generating output images in the radiographic image processing apparatus.

The flow of the to-be-output image generating process is described with reference to the flowchart in FIG. 2. The process is performed by the controller 51 of the console 50 after imaging the subject S.

When the subject S is irradiated with X-rays from the X-ray emitter 20 and the FPD 30 generates image data of the subject S, the controller 51 obtains the image data from the FPD 30 via the inputter 52 (Step S101).

The controller 51 stores the obtained image data in the storage 53 and causes the display 54 to display the obtained image in the image display section 5411 (shown in FIG. 3, FIG. 4, FIG. 5) based on the obtained image data (Step S102).

Figure 3:
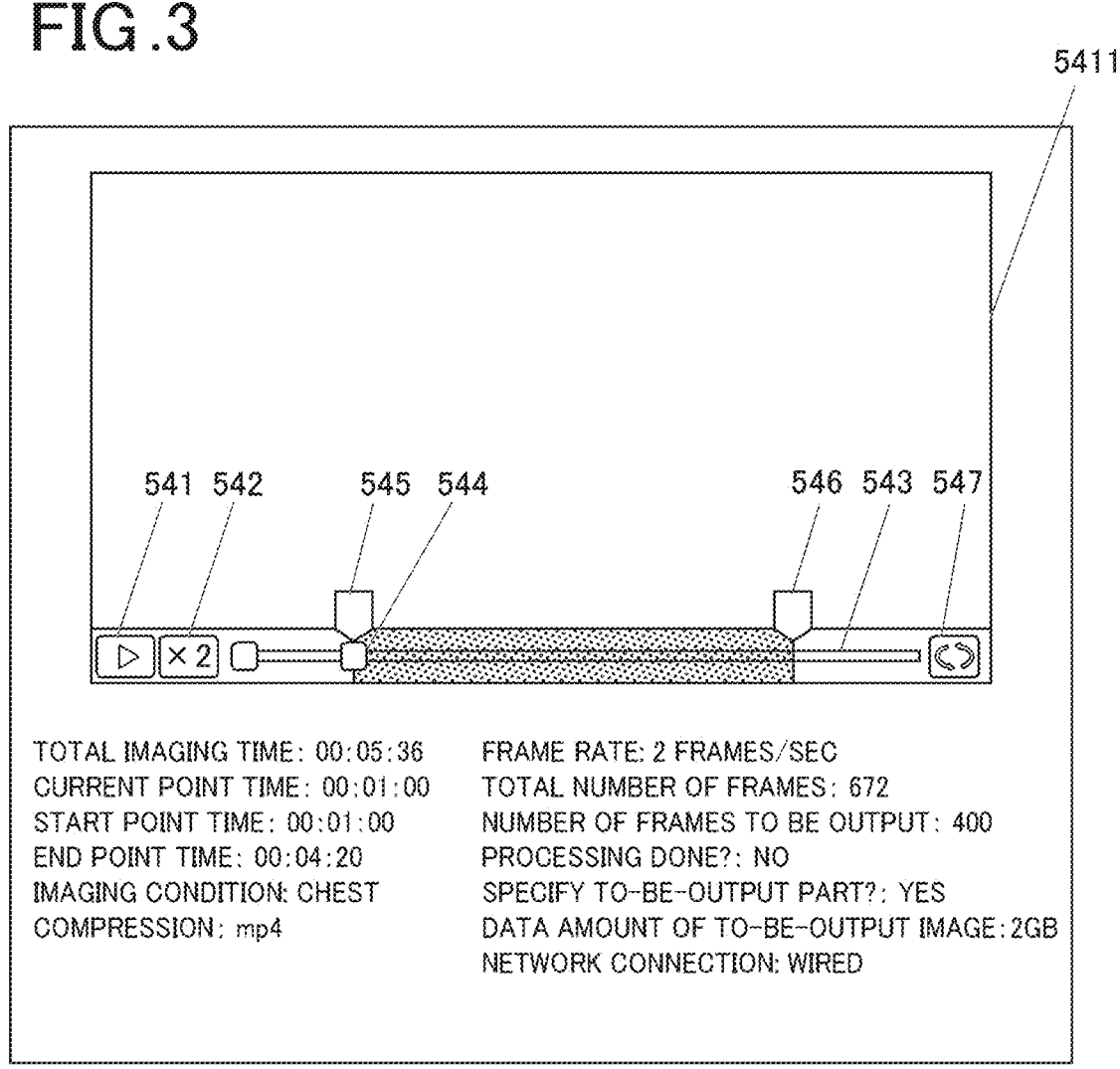
FIG. 3 shows contents displayed on a display.

The controller 51 also causes the display 54 to display a play button 541, a double-speed button 542, an axis 543, a current point 544, a start point 545, an end point 546, a repeat button 547, and so forth, as shown in FIG. 3.

The controller 51 determines whether or not specification of the to-be-output image part is enabled (Step S103). When determining that specification of the to-be-output image part is enabled (Step S103: YES), the controller 51 proceeds to Step S104. When determining that specification of the to-be-output image part is not enabled (Step S103: NO), the controller 51 proceeds to Step S105.

The method of determining whether or not specification of the to-be-output image part is enabled by the console 50 is described later.

The operator specifies the to-be-output image part by operating the operation receiver 55 (Step S104). When the operator specifies the to-be-output image part, the controller 51 determines the to-be-output image part. When the operator does not specify the to-be-output image part, the controller 51 repeats Step S104.

The method of specifying the to-be-output part by the operator is described later.

In externally recording the to-be-output image part, the image processor 56 performs processing on the to-be-output image part of the image data determined by the controller 51 in Step S104 (Step S105). The processing is performed in accordance with requirements of the external device 60 to which the image data is output.

The controller 51 outputs the image data on which processing is performed in Step S105 to the external device 60 via the communication unit 57 (Step S106).

In this embodiment, the operator selects the image data that is considered to be necessary for diagnosis in Step 104, and the selected image data is subject to image processing in Step S105. This can reduce system load and enables efficient output of image data.

<Method of Setting Whether Specification of To-Be-Output Image Part is Enabled>

The operator can set, by operating the operation receiver 55, whether or not specification of the to-be-output image part is enabled according to the external device 60 to which the image data is output. More specifically, the operator can set whether or not specification of the to-be-output image part is enabled depending on whether the external device 60 is an analysis device or an image storing device. There are a case where all the frames are used for image analysis and a case where part of the image/dynamic image is selected and directly used for diagnosis. Whether specification of the to-be-output image part is enabled can be determined on the basis of the type of the external device 60. The operator can avoid being confused by devices to which the image data is output. The operator can set beforehand that the entire image data is output to an analysis device (i.e., image data cannot be narrowed down) or that part of the image data is output to a storing device.

Further, by operating the operation receiver 55, the operator can set whether or not specification of the to-be-output image part is enabled according to the connection state (wired/wireless connection, radio wave state) of the console 50 to the network. When the console 50 is wirelessly connected to the network, the operator can consider transfer time of the image data and determine only that specification of the to-be-output image part is enabled. On the other hand, when the console 50 is connected to the network through a cable, the operator can determine either specification of the to-be-output image part is enabled or disabled.

In Step S103, the controller 51 determines whether or not specification of the to-be-output image part is enabled on the basis of the setting by the operator.

Further, by operating the operation receiver 55, the operator can set whether or not specification the to-be-output image part is enabled according to imaging conditions. This allows the operator to specify the to-be-output image part according to imaging conditions without confusion and mistakes. More specifically, when the moving image shows the chest part, the operator can determine that the entire image data is output. On the other hand, when the image is for orthopedics, the operator can determine that part of the image data is output.

In Step S103, the controller 51 determines whether or not specification of the to-be-output image part is enabled on the basis of the setting by the operator. The controller 51 thus functions as a first determining unit.

The operator can set, by operating the operation receiver 55, whether or not specification the to-be-output image part is enabled according to whether image processing has been performed on the image data. This allows the operator to specify the to-be-output image part without confusion and mistakes on the basis of whether image processing has been done. Image processing is performed on image data that is to be visually checked by the user. On the other hand, image processing is not performed on image data that is used for analysis. The image for analysis is used without being processed. The operator can determine that specification of the to-be-output image part is disabled for an image on which image processing has been performed and that specification of the to-be-output image part is enabled for an image on which image processing has not been performed.

In Step S103, the controller 51 determines whether or not specification of the to-be-output image part is allowed on the basis of the setting by the operator. The controller 51 thus functions as a second determining unit.

<Method of Specifying To-Be-Output Image Part>

FIG. 3 shows a detailed example of the contents displayed on the display 54 when the operator specifies the to-be-output image part (Step S104).

When the play button 541 is pressed, the obtained image is played. Consecutively-obtained images are displayed and played as a dynamic image on the image display section 5411.

When the double-speed button 542 is pressed while the dynamic image is being played with the play button 541, the speed of playing the dynamic image is doubled.

The frame that corresponds to the current point 544 on the axis 543 is displayed on the image display section 5411. By selecting and sliding the current point 544, a desired frame in the dynamic image is displayed.

The start point 545 indicates the start point of the playing part of the dynamic image. When the start point 545 is selected, the frame at the start point is displayed on the image display section 5411.

The end point 546 indicates the end point of the playing part of the dynamic image. When the end point 546 is selected, the frame at the end point is displayed on the image display section 5411.

Part of the axis 543 corresponding to the playing part (from the start point 545 to the end point 546) is shown in a deeper color than the other part of the axis 543 corresponding to the not-playing part, for example.

The default positions of the start point 545 and the end point 546 are set in accordance with a protocol in which the imaging time is determined. For example, when the imaging time is set to 5 minutes in the protocol and the actual imaging time is 10 minutes, the default start point 545 is set at zero time and the default end point 546 is set at 5 minutes.

The repeat button 547 is for repeating playing the frames within the playing part of the dynamic image.

The display 54 also displays the imaging time, the time at the selected point (current point 544, start point 545, and end point 546), volume of the specified to-be-output part of the dynamic image, the connection state of the console 50 (wired/wireless connection, radio wave state), the number of frames in the to-be-output image part, and the total number of obtained frames.

Herein, the maximum number of frames in the specified to-be-output image part may be set according to the connection state (wired/wireless connection, radio wave state) of the console 50 from which the image data is sent. For example, assume that the console 50 is in an instrument carriage and wirelessly connected to an intra-facility system (external device 60) and that the connection is weak. In the case, the maximum number of frames may be set to 80 out of 100 frames in total.

In Step S104, the operator specifies the to-be-output image part of the dynamic image by sliding (moving) the start point 545 and the end point 546 on the axis 543 in the display 54 shown in FIG. 3.

The method of specifying the to-be-output image part is described in detail.

The operator can specify, by operating the operation receiver 55, the to-be-output image part of the dynamic image by specifying the first frame and the last frame of the to-be-output image part. The operator sets the start point 545 to the frame from which the to-be-output image part starts and sets the end point 546 to the frame at which the to-be-output image part ends, while checking the display 54. The operator can check the dynamic image and specify the to-be-output image part as desired. Accordingly, only necessary image part for diagnosis is output.

Further, the operator can specify, by operating the operation receiver 55, the to-be-output image part of the dynamic image by specifying the imaging time. When the start point 545/end point 546 is moved, the time corresponding to the start point/end point changes. By setting the start point 545/end point 546 at the desired start time/end time, the operator can specify the to-be-output image part along the imaging time.

The start time and the end time may be directly input to "start point time" and "end point time" in FIG. 3.

Further, the operator can specify, by operating the operation receiver 55, the to-be-output image part of the dynamic image according to a predetermined image volume that can be output (e.g., up to 3 GB). When the volume of the to-be-output image part exceeds the predetermined image volume, the display 54 displays an error message, or the start point 545 and/or the end point 546 becomes unable to be slided/moved beyond the predetermined image volume.

Further, the operator can specify, by operating the operation receiver 55, the to-be-output image part of the dynamic image according to the connection state of the console 50, from which the image data is sent, to the network (wired/wireless connection, radio wave state). This enables smooth transfer of the dynamic image to an image storing device when the console 50 is wirelessly connected to the network and the transfer speed is slow, for example. When the transfer speed is slow and the volume of the to-be-output image part exceeds the predetermined image volume, the display 54 displays an error message. The maximum image volume may be changed, for example, by switching the modes between the mode 1: maximum image volume is 1 GB and the mode 2: maximum image volume is 3 GB according to the transfer speed (e.g., whether the connection is through wire or wireless).

Further, the operator can specify, by operating the operation receiver 55, the to-be-output image part of the dynamic image from which a failure part is excluded. The failure part in the obtained dynamic image is automatically identified. This allows the operator to avoid failing to identify the failure part and to smoothly specify the to-be-output image part. The automatic identification of the failure part is done through image analysis by the console 50. For example, assume that the dynamic image shows the chest part. When part of the lungs or other important part is missing in a frame, the controller 51 can automatically determine that the frame is a failure frame. When a frame is blurred, the controller 51 can also automatically determine that the frame is a failure frame.

Herein, specification of the to-be-output image part may be disabled when multiple failures are automatically identified at different time points. For example, when failures are automatically identified at 3 seconds past and at 7 seconds past in 10-second imaging time, specification of the to-be-output image part is disabled. This is because the to-be-output image part may not contain enough normal frames and therefore may not be usable for diagnosis when multiple failures are identified at different time points. In such a case, a message may be displayed that specification of the to-be-output image part is disabled.

Figure 4:
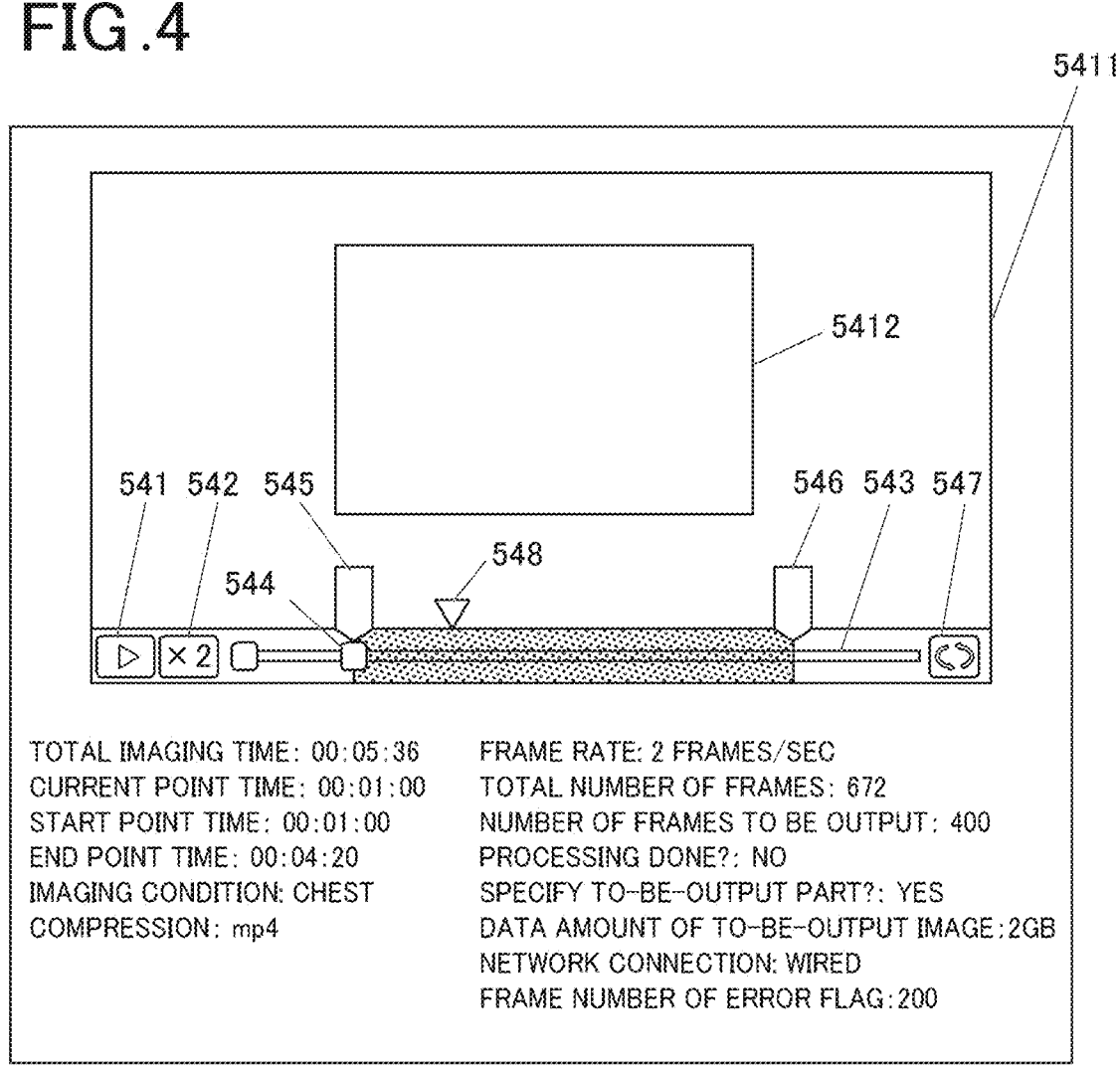
FIG. 4 shows the display showing an error flag and a clipping region of an image.

Further, the operator can specify, by operating the operation receiver 55, the to-be-output image part of the dynamic image without excluding an automatically-identified failure image(s). More specifically, the operator can specify the to-be-output image part in consideration of the error flag 548 in FIG. 4 that indicates a failure image. The operator thus can smoothly specify the to-be-output image part. For example, as shown in FIG. 4, the operator can set the start point 545/end point 546 while keeping a failure frame noticeable at a glance with the error flag 548. Alternatively, the operator can exclude the failure frame from the to-be-output image part.

When the error flag 548 is selected, the frame indicated by the error flag 548 is displayed on the image display section 5411. The information on the frame indicated by the error flag 548 is also displayed on the display 54. Such information includes the frame number indicated by the error flag 548, for example. This allows the operator to recognize the quantitative information on the frame indicated by the error flag 548 and avoid mistaking failure frames.

Further, by operating the operation receiver 55, the operator can specify the to-be-output image part of the dynamic image and reduce the number of frames in the to-be-output image part such that the frame rate of the to-be-output image part is less than the frame rate of the obtained dynamic image. More specifically, when the operator inputs a numerical value in "frame rate" shown on the display 54 in FIG. 3, the frames are thinned out so as to match the input frame rate. Thus, the number of frames to be stored in the image storing device or the analysis device are reduced. This can reduce system load.

Herein, the frame rate may be automatically set by the controller 51 according to the connection state (wired/wireless connection, radio wave state) of the console 50 to the network. For example, the controller 51 sets the frame rate such that the frame rate under wireless connection is lower than the frame rate under connection through wire.

Further, by operating the operation receiver 55, the operator can specify the to-be-output image part of the dynamic image and then specify the clipping region 5412 in each frame and/or a certain frame of the to-be-output image part. The operator is thus allowed to specify the to-be-output image part in the spatial axis (i.e., clipping region 5412) as well as in the temporal axis. Accordingly, the operator can specify only a part necessary for diagnosis. The image volume to be stored in the image storing device or the analysis device is therefore reduced. This can reduce system load.

Further, by operating the operation receiver 55, the operator can specify the to-be-output image part of the dynamic image on the basis of information on the number of frames shown on the display 54 in FIG. 3. The information includes the number of frames constituting the to-be-output image part and the number of all the frames. By quantitatively recognizing the to-be-output image part (i.e., the number of frames to be output), the operator can avoid wrongly specify the to-be-output image part.

Further, by operating the operation receiver 55, the operator can specify the to-be-output image part of the dynamic image within the part notified by the external device 60 (e.g., analysis system). More specifically, the controller 50 can obtain the image part output in the past from the external device 60 via the communication unit 57, so that the image part output in the past is applied to the current to-be-output image part. The controller 51 thus can determine the to-be-output image part. By receiving feedback from the external device 60 on the region used for diagnosis (e.g., region clipped in the spatial and temporal axis direction in the previous imaging), the controller 51 can specify appropriate to-be-output image part.

Further, by operating the operation receiver 55, the operator can specify the part that is not to be output. The part not to be output is shown in a light color in FIG. 5. This can increase usability of various operators.

Figure 5:
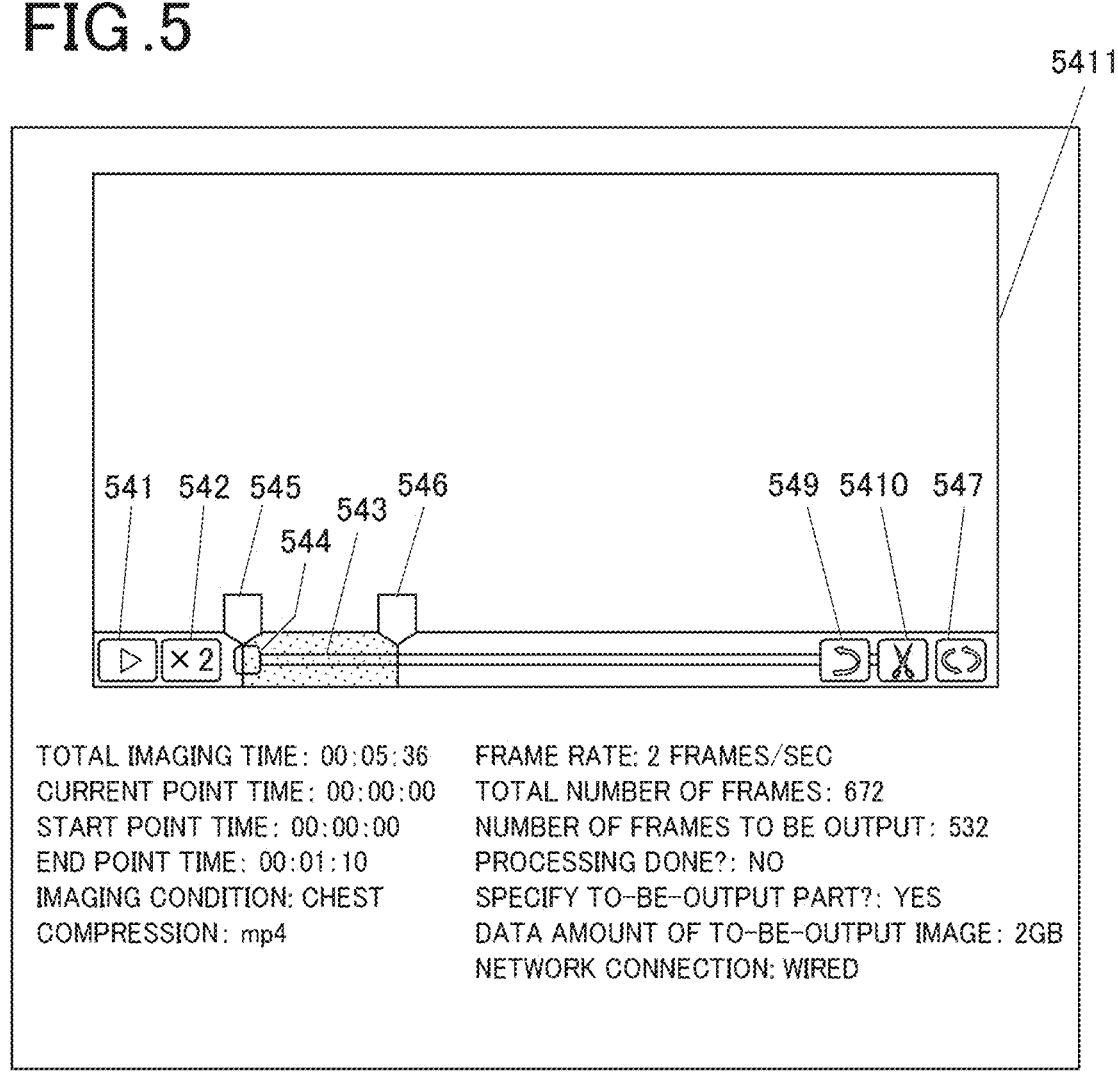
FIG. 5 shows the display in which the part not to be output is specified.

The operator can also cut off the part that is not to be output using a cut button 5410 shown in FIG. 5. The cutting operation can be undone with an undo button 549.

Among the above methods of specifying the to-be-output image part, one or more methods may be used. For example, in using multiple methods, a failure part is removed and frames constituting the to-be-output image part are thinned out.

Although some embodiments of the present invention have been described and illustrated in detail, the scope of the present invention is not limited to the embodiments described above but encompasses the scope of the invention recited in the claims and the equivalent thereof.

The present disclosure aims to efficiently output moving image data to an external device while reducing system load. However, when system load is light, data of all the obtained images may be output after outputting the specified to-be-output image data. For example, system load of the system (CPU) may be monitored after the to-be-output image part is specified. When the load is at a certain low level, data of all the frames may be output. As another example, after a certain time has passed since the output of the to-be-output image part, data of all the frames may be output.

Although embodiments of the present invention have been described and illustrated in detail, the disclosed embodiments are made for purposes of illustration and example only and not limitation. The scope of the present invention should be interpreted by terms of the appended claims.

What is claimed is:

1. A radiographic image processing apparatus comprising:
a hardware processor that obtains moving image data captured by a radiographic imaging apparatus, causes a display to display a moving image based on the moving image data, and specifies a part of the moving image data that is to be output to an external device; and
an image processor that performs image processing only on the part of the moving image data, wherein the hardware processor outputs, to the external device, the part of the moving image data on which the image processing has been performed by the image processor, wherein the hardware processor specifies the part by automatically identifying a failure part in the moving image data and excluding the failure part from the moving image data.

2. The radiographic image processing apparatus according to claim 1, wherein the hardware processor specifies the part by determining a first frame and a last frame of the part.

3. The radiographic image processing apparatus according to claim 1, wherein the hardware processor specifies the part by determining a clipping region in a frame constituting the moving image.

4. The radiographic image processing apparatus according to claim 1, wherein the hardware processor reduces a frame rate of the part of the captured moving image, the frame rate being reduced by reducing a number of frames constituting the captured moving image.

5. The radiographic image processing apparatus according to claim 1, wherein the hardware processor determines whether or not specification of the part is enabled, based on whether or not the image processor has performed image processing on the moving image data.

6. The radiographic image processing apparatus according to claim 1, wherein the image processor generates compressed image data in a moving image format by compressing the part of the moving image data.

7. The radiographic image processing apparatus according to claim 1, wherein the hardware processor causes the display to display information on
- a number of frames constituting the part of the moving image and
- a number of all frames constituting the captured moving image.

8. The radiographic image processing apparatus according to claim 1, wherein the hardware processor plays a moving image based on the part of the moving image data.

9. A radiographic image processing method comprising:
- obtaining moving image data captured by a radiographic imaging apparatus;
- causing a display to display a moving image based on the moving image data;
- specifying the part by automatically identifying a failure part in the moving image data and excluding the failure part from the moving image data;
- specifying the part of the moving image that is to be output to an external device;
- performing image processing only on the part of the moving image data; and
- outputting, to the external device, the part of the moving image data on which the image processing has been performed.

10. A non-transitory computer-readable storage medium storing a program that causes a computer of a radiographic image processing apparatus to:
- obtain moving image data captured by a radiographic imaging apparatus;
- cause a display to display a moving image based on the moving image data;
- specify the part by automatically identifying a failure part in the moving image data and excluding the failure part from the moving image data;
- specify the part of the moving image that is to be output to an external device;
- perform image processing only on the part of the moving image data; and output, to the external device, the part of the moving image data on which the image processing has been performed.

11. A radiographic image processing apparatus comprising:
- a hardware processor that obtains moving image data captured by a radiographic imaging apparatus, causes a display to display a moving image based on the moving image data, and specifies a part of the moving image data that is to be output to an external device; and
- an image processor that performs image processing only on the part of the moving image data, wherein the hardware processor outputs, to the external device, the part of the moving image data on which the image processing has been performed by the image processor, wherein the hardware processor causes the display to display information on a number of frames constituting the part of the moving image and a number of all frames constituting the captured moving image, and wherein the hardware processor specifies the part by automatically identifying a failure part in the moving image data and excluding the failure part from the moving image data.

* * * * *